(12) United States Patent
Kierulf et al.

(10) Patent No.: US 8,827,909 B2
(45) Date of Patent: Sep. 9, 2014

(54) ULTRASOUND PROBE

(75) Inventors: Trond Kierulf, Asgardstrand (NO);
Anders Herman Torp, Oslo (NO)

(73) Assignee: General Electric Company, Schenectady, NY (US)

( * ) Notice: Subject to any disclaimer, the term of this patent is extended or adjusted under 35 U.S.C. 154(b) by 206 days.

(21) Appl. No.: 13/347,928

(22) Filed: Jan. 11, 2012

(65) Prior Publication Data

US 2013/0178744 A1    Jul. 11, 2013

(51) Int. Cl.
*A61B 8/14* (2006.01)

(52) U.S. Cl.
USPC .......................................... 600/459; 600/437

(58) Field of Classification Search
None
See application file for complete search history.

(56) References Cited

U.S. PATENT DOCUMENTS

| | | | |
|---|---|---|---|
| 5,305,017 A | 4/1994 | Gerpheide | |
| 8,388,541 B2 * | 3/2013 | Messerly et al. | 600/462 |
| 2002/0138007 A1 * | 9/2002 | Nguyen-Dinh et al. | 600/459 |
| 2006/0058654 A1 * | 3/2006 | Di Marco et al. | 600/437 |
| 2009/0156926 A1 * | 6/2009 | Messerly et al. | 600/409 |
| 2009/0276515 A1 * | 11/2009 | Thomas et al. | 709/223 |
| 2010/0010348 A1 * | 1/2010 | Halmann | 600/443 |
| 2010/0063398 A1 * | 3/2010 | Halmann et al. | 600/459 |
| 2010/0145195 A1 * | 6/2010 | Hyun | 600/437 |
| 2010/0160786 A1 | 6/2010 | Nordgren et al. | |
| 2010/0191120 A1 * | 7/2010 | Kraus et al. | 600/459 |
| 2010/0217128 A1 * | 8/2010 | Betts | 600/459 |
| 2011/0224552 A1 * | 9/2011 | Poland et al. | 600/459 |

OTHER PUBLICATIONS

Apple, Magic mouse: Suddenly, everything clicks. And swipes. And scrolls, Nov. 22, 2011, 3, http://www.apple.com/magicmouse/.
GE Healthcare, Ultrasound VScan, GE Healthcare Ultrasound VScan, Nov. 11, 2011, 1, http://vscanultrasound.gehealthcare.com/products/vscan.

* cited by examiner

*Primary Examiner* — Long V. Le
*Assistant Examiner* — Bradley Impink
(74) *Attorney, Agent, or Firm* — Rathe Lindenbaum LLP

(57) ABSTRACT

An ultrasound probe comprises a body terminating at a nose, an ultrasound transducer adjacent the nose and facing a first direction, and a touchpad zone to detect a sliding gesture of a first digit. The first touchpad zone extends along a first surface facing a second direction perpendicular to the first direction.

22 Claims, 5 Drawing Sheets

ULTRASOUND PROBE

BACKGROUND

Ultrasound or ultrasonography is a medical imaging technique that utilizes high-frequency (ultrasound) waves and their reflections. Such ultrasound waves are directed into a person's anatomy using a handheld probe. A separate host device typically provides controls for the operation of the probe, while receiving and displaying results from the probe. Adjusting the controls on the host while also manipulating the probe to optimally position the probe is not intuitive and often challenging.

DETAILED DESCRIPTION OF THE EXAMPLE EMBODIMENTS

Figure 1:
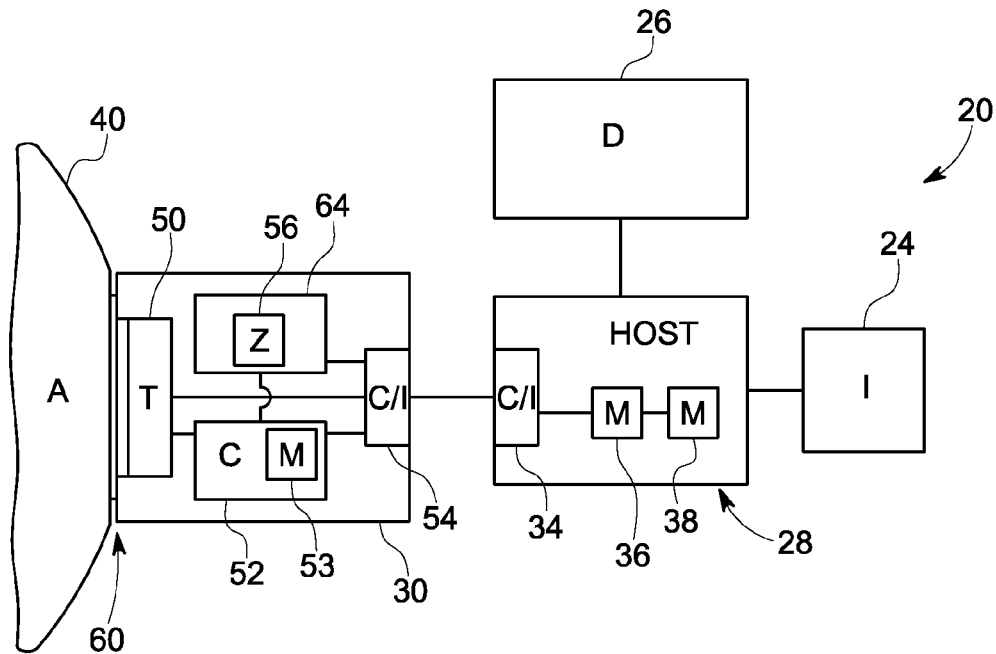
FIG. 1 is a schematic illustration of an example ultrasound sensing system.

FIG. 1 schematically illustrates an example ultrasound system 20. As will be described hereafter, ultrasound system 20 provides an intuitive method by which the operation of an ultrasound probe and/or the presentation of the ultrasound results may be adjusted and controlled. Ultrasound system 20 comprises input 24, display 26, host 28 and probe 30.

Input 24 comprises a device by which a person may provide selections, commands or instructions to host 28. Input 24 may comprise a keyboard, a mouse, a microphone with speech recognition software, a keypad and the like. Input 24 may be incorporated as part of a monitor which provides host 28. Input 24 may also be Incorporated as part of display 26, wherein display 26 comprises a touch screen. Alternatively, input 24 may comprise one or more separate input structures in communication with host 28 in a wired or wireless fashion. In some implementations, input 24 may be omitted.

Display 26 comprises a screen or other display by which the results from probe 30 are visibly presented to a caretaker, such as a doctor or nurse. In one implementation, display 26 may comprise a separate screen distinct from host 28 and in communication with host 28 in a wired or wireless fashion. In another implementation, display 26 may be Incorporated as part of host 28 as part of a single self-contained unit.

Host 28 comprises a monitor or other unit which analyzes signals from probe 30 and presents the results of the analysis as well as the signals themselves on display 26. In some implementations, host 28 may additionally at least partially control probe 30.

Host 28 comprises communication interface 34, controller 36 and memory 38. Communication interface 34 comprises an interface by which host 28 communicates with probe 30. In one implementation, communication interface 34 facilitates wireless communication. For example, in one implementation, communication interface 34 comprises a wireless antenna. In another implementation, communication interface may comprise optical communication technology, such as an infrared transmitter. In another implementation, to communication interface 34 facilitates a wired communication such as through a cable. For example, communication interface may comprise a USB port or other communication port.

Controller 36 comprises one or more processing units configured to generate control signals in accordance with instructions contained in memory 38. For purposes of this application, the term "processing unit" shall mean a presently developed or future developed processing unit that executes sequences of instructions contained in a memory 38. In the example illustrated, memory 38 comprises a non-transient computer-readable medium containing computer code for the direction of controller 36. Execution of the sequences of instructions causes the processing unit comprising controller 36 to perform steps such as generating control signals. The instructions may be loaded in a random access memory (RAM) for execution by the processing unit from a read only memory (ROM), a mass storage device, or some other persistent storage. In other embodiments, hard wired circuitry may be used in place of or in combination with software instructions to implement the functions described. For example, controller 36 may be embodied as part of one or more application-specific integrated circuits (ASICs). Unless otherwise specifically noted, the controller is not limited to any specific combination of hardware circuitry and software, nor to any particular source for the instructions executed by the processing unit.

According to one implementation, controller 36, following instructions contained in memory 38, receives ultrasound echo signals from probe 30 and analyzes such signals, wherein the results of such analysis are presented on display 26. In some implementations, controller 36 may generate control signals adjusting or varying the display of signals and/or results on display 26. In some implementations, controller 36 may further generate control signals adjusting the operation of probe 30. As will be described hereafter, at least a portion of some control functions over probe 30 or over the visible presentation on display 26 are controlled by manual inputs provided on probe 30 itself.

Probe 30 comprises a handheld instrument by which ultrasound waves or pulses are directed into anatomy 40 and by which reflections of such waves are sensed to produce signals which are transmitted to host 28. Probe 30 provides an intuitive means by which the control of probe 30 and the presentation results on display 26 may be adjusted, permitting a physician or caretaker to focus his or her attention on the patient. Probe 30 comprises transducer 50, controller 52, communication interface 54 and touch zone 56.

Transducer 50 comprises an ultrasound device located at a front end or nose 60 of probe 30 that is configured to emit and receive high-frequency sound waves (ultrasonic waves). During imaging by system 20, the nose 60 of probe 30 may be placed upon or against the exterior of anatomy 44, or may be partially inserted into anatomy 40 depending upon those portions of the anatomy which are to be imaged. In one implementation, transducer 50 comprises quartz crystals, piezoelectric crystals, that change shape in response to the application electrical current so as to produce vibrations or sound waves. Likewise, the impact of sound or pressure waves upon such crystals produce electrical currents. As a result, such crystals are used to send and receive sound waves. Transducer 50 may additionally include a sound absorbing substance to eliminate back reflections from the probe itself and an acoustic lens to focus emitted sound waves.

Controller 52 comprises one or more processing units contained in probe 30 and configured to generate control signals in response to sensed signals received by touch zone 56 and according to instructions contained in memory 62. One implementation, memory 52 comprises a non-transitory computer-readable medium providing persistent storage for such instructions or code. In one implementation, memory 52 may comprise software. In another implementation, memory 53 may comprise an application-specific integrated circuit (ASIC). In the example illustrated, controller 52 generate control signals in response to sensed signals received from touch zone 56, wherein such control signals are transmitted to transducer 50 to adjust the operation of transducer 50. For example, in response to receiving signals from touch zone 56, controller 52 may generate control signals causing the frequency of waves emitted and detected by transducer 52 be adjusted so as to vary a depth at which the anatomy is being sensed. In the example illustrated, controller 52 also generates control signals in response to sensed signals from touch zone 56 to adjust the presentation of sensing results on display 26. For example, in response to receiving signals from touch zone 56, controller 52 may generate control signals which are transmitted to host 28 would cause host 28 to vary the display of information upon display 26.

Communication interface 54 comprises an interface by which probe 30 communicates with host 28. In one implementation, communication interface 54 facilitates wireless communication. For example, in one implementation, communication interface 54 comprises a wireless antenna. In another implementation, communication interface may comprise optical communication technology, such as an infrared transmitter. In another implementation, communication interface 54 facilitates a wired communication such as through a cable. For example, communication interface 54 may comprise a USB port or other communication port.

Touch zone 56 comprises a tactile touchpad or trackpad (also sometimes referred to as a glide point or touch sensitive input device) extending along and external surface 64 of probe 30. Touch zone 56 is configured to detect or sense motion and position of person's digit such that touch zone 56 may detect a sliding gesture of one or more digits. Because touch zone 56 is configured to detect a sliding gesture (in contrast to being configured to merely detect a tap or depressment), touch zone 56 is able to receive manual input or manual commands from a caretaker's hands without the caretakers fingers having to be displaced or separated from probe 30. Different commands or different inputs may be manually entered without a caretaker (sonographer) having to lift his or her finger and appropriately position his or her finger on a selected or particular spot on probe 30. As a result, the caretaker need not be concerned about the position of his or her finger on the probe when entering a command, minimizing the need for the caretaker to glance at the probe or at the position of his or her hand or finger prior to entering a command. The caretaker may continuously hold the probe 30 to reposition probe 30 while the caretaker continuously positions his or her finger against touch zone 56 and simply moves his or her finger to adjust the operation of probe 30 or display 26. Thus, the caretaker may focus his or her attention on the patient or on the display screen presenting the ultrasound results.

Figure 2:
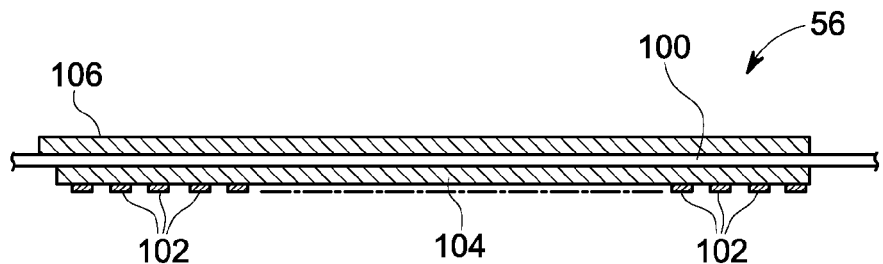
FIG. 2 is a sectional view of a tactile sensing device of an example probe of the ultrasound sensing system of FIG. 1.

In one implementation, touch zone 56 comprise a capacitive-based sensor in which the capacitive virtual ground effect of a finger or the capacitance between sensors is sensed. In one implementation, touch zone 56 utilizes a matrix approach in which a series of conductors are arranged array of parallel lines into layers separated by an insulator and crossing each other at right angles to form a grid. FIG. 2 is a sectional view illustrating one example construction for touch zone 56. As shown by FIG. 2, touch zone 56 comprises electrode strips 100, 102, insulator substrate 104 and overlay insulator 106. Electrode strips 100, 102 each comprise a set of multiple parallel strips of electrically conductive material on opposite sides of insulator substrate 104. Electrode strips 100 cross one another at right angles to form a grid. Its status of your 104 comprises a layer of electrically insulating material between strips 100, 102. Overlay insulator 106 comprise a layer of electrically insulating material which overlies strips 100 and protects the electrode strips from corrosion and wear.

In operation, high-frequency signals applied sequentially between pairs of strips in the two-dimensional grid array of strips 100, 102. The current is passed between the nodes is proportional to capacitance. Positioning of a finger over one of the intersections between the conductive layer forms a virtual ground by which some electrical field is shunted. This results in a change in apparent capacitance at this location, wherein the change in apparent capacitance is sensed to detect movement and positioning of a person's or fingers.

Another implementation, custom 56 may alternatively utilize a capacitive shunt method, wherein changes in capacitance between a transmitter and a receiver on opposite sides of a sensor are detected. In such an implementation, a transmitter great electric fields oscillate at 200 300 kHz. When the fingers placed between the transmitter and receiver, it serves as a ground point by which some of the field lines are shunted away to decrease apparent capacitance. This capacitance is sensed to detect movement of the person's fingers.

In yet other implementations, touch zone 56 may alternatively utilize conductive sensing technology. In still other embodiments, touch zone 56 may utilize other future developed technologies wherein custom 56 is configured to detect a sliding gesture or movement of a person's finger along the zone 56 while the person's finger remains in contact with touch zone 56.

Figure 3:
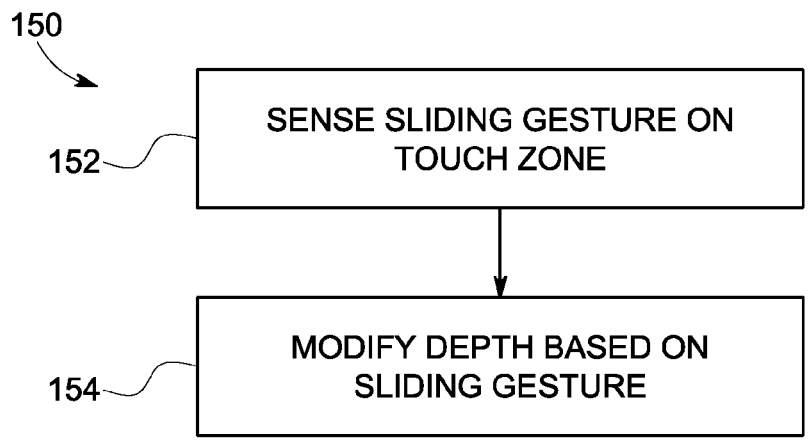
FIG. 3 is a flow diagram of an example method that may be carried out by the system of FIG. 1.

FIG. 3 is a flow diagram illustrating an example method 150 and may be carried out by ultrasound sensing system 20 of FIG. 1. As indicated by step 152, controller 52, following instructions contained in memory 53, generates control signals causing sliding movement or a sliding gesture of a person's finger along touch zone 56 to be detected. As noted above, in one implementation in which a capacitance type tactile sensing is employed, controller 56 causes high-frequency electrical signals to be transmitted between pairs of strips 100, 102 (shown in FIG. 2). In implementation other types of tactile sensing technologies employed, controller 52 may perform other functions.

As indicated by step 154, based upon the sensed sliding gesture of a person's finger or fingers against and along touch zone 56, the depth of sensing by probe 30 is adjusted. In other words, the characteristics (such as frequency) of the ultrasonic waves being emitted in detected by transducer 50 is adjusted to image different interior portions of anatomy 40. For example, a sliding gesture in a first direction may cause the depth to be increased, light sliding gesture in a second direction because the depth to be decreased. A sliding gesture having a first shape or path along touch zone 56 may cause the depth be increased, while a sliding gesture having a second different shape or movement along a second different path may cause the depth to be decreased.

In one implementation, in response to sensing such a sliding gesture along touch zone 56, controller 52 generates transducer control signals which are transmitted directly to transducer 50 to adjust the operation of transducer 50 so as to adjust the sensing depth. In another implementation, in response to sensing such a sliding gesture along touch zone 56, controller 52 communicates the detected sliding gesture to host 28, wherein controller 36 of host 38 uses the detected sliding gesture to generate transducer control signals which are transmitted to transducer 50 for adjusting the depth of sensing by transducer 50.

In other implementations, particular sliding gestures of a person's finger or fingers along touch zone 56 may correspond to other commands or inputs. For example, in some implementations, such sliding gestures may be utilized by system 20 to cause the presentation of ultrasound results on display 26 to be adjusted. For example, such sliding gestures may be utilized to activate a zoom function or to move a color flow region of interest bounding box (or a bounding box with other type of data being displayed) within a displayed one, two, three or four dimensional image. In some implementations, other characteristics of probe 30 itself may be adjusted by such a sliding gesture such as a focus, width or direction of emitted and sensed ultrasound pulses.

In yet other implementations, ultrasound sensing system 20 may utilize other interactions with touch zone 56 to facilitate control of probe 30 and/or display 26. For example, ultrasound sensing system 20 may additionally facilitate the entry of commands utilizing other non-sliding gestures such as tapping against touch zone 56. In such implementations, the use of interactions where the person finger or fingers are temporarily withdrawn from the surface 64, such inputs may be relegated to less time sensitive commands or commands that are less frequently utilized.

Figure 4:
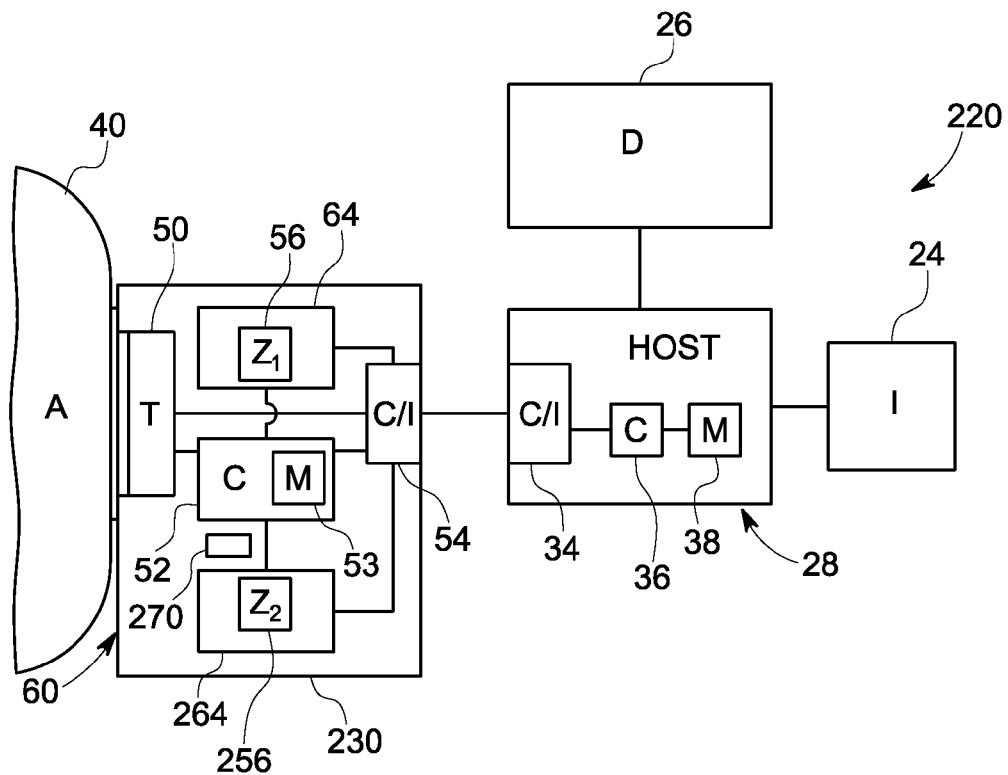
FIG. 4 is a schematic illustration of another example of the ultrasound sensing system of FIG. 1.

FIG. 4 schematically illustrates ultrasound sensing system 220, another example implementation of ultrasound sensing system 20. Ultrasound sensing system 220 is similar to ultrasound sensing system 20 except that system 220 includes probe 230 in place of probe 30. Probe 230 is itself similar to probe 30 except that probe 230 includes touch zone 256 ($Z_2$) in addition to that zone 56 ($Z_1$). For ease of illustration, those remaining components of ultrasound sensing system 220 which correspond to components of ultrasound sensing system 20 are numbered similarly.

Touch zone 256 is similar to touch zone 56 except that touch zone 256 extends along an external surface 264 of probe 230. In the example illustrated, nose 60 and transducer 50 face in a first direction. Surface 64 and touch zone 56 face in a second direction nonparallel, and nominally perpendicular, to the first direction in which nose 60 and transducer 50 face. Surface 264 and touch zone 256 face in a third direction nonparallel, and nominally perpendicular, to the first direction 60 and transducer 50 face and also nonparallel, and nominally perpendicular, to the second direction in which surface 64 and touch zone 56 face. As a result, touch zones 56 and 256 facilitate the receipt of sliding gestures from the caretaker's index finger and thumb. In some implementations, because the zones 56 and 256 face outwardly in directions perpendicular to one another, zones 56 and 256 facilitate the entry of commands using different digits while also facilitating the continued gripping and holding of probe 230 in space (solely supported or suspended by the caretaker's hand, not relying upon an underlying surface for support) by the same digits. Separate commands or commands based upon a combination of sliding gestures received from both the finger and the thumb may be entered utilizing zones 56 and 256.

In one implementation, touch zones 56 and 256 are spaced apart from one another by an insensitive zone or surface area 270 between surfaces 64 and 264. As a result, ultrasound sensing system 220 may distinguish between sensed sliding gestures received by touch zone 56 versus those gestures sensed on touch zone 256. In other words, different touch zones may be dedicated to different inputs such that the same gesture may be input to the different zones but may have different results or a different impact depending upon which zone from which the sliding gesture was sensed. In other implementations, touch zones 56 and 256 may be continuous with respect to one another along a surface of probe 230.

Figure 5:
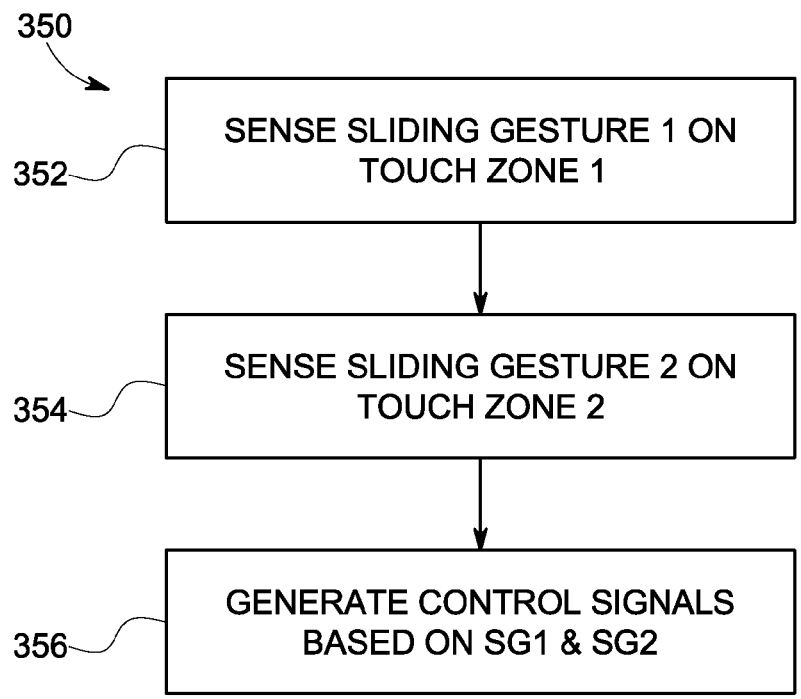
FIG. 5 is a flow diagram of an example method that may be carried out by the system of FIG. 4.

FIG. 5 is a flow diagram illustrating an example method 350 that may be carried out by ultrasound sensing system 220 shown in FIG. 4. As indicated by step 352, controller 52, following instructions contained in memory 53, generates control signals causing sliding movement or a sliding gesture of a person's finger along touch zone 56 to be detected. As noted above, in one implementation in which a capacitance type tactile sensing is employed, controller 56 causes high-frequency electrical signals to be transmitted between pairs of strips 100, 102 (shown in FIG. 2) of touch zone 56. In implementation other types of tactile sensing technologies employed, controller 52 may perform other functions.

As indicated by step 354, controller 52, following instructions contained in memory 53, generates control signals causing sliding movement or a sliding gesture of a person's finger along touch zone 256 to be detected. As noted above, in one implementation in which a capacitance type tactile sensing is employed, controller 56 causes high-frequency electrical signals to be transmitted between pairs of strips 100, 102 (shown in FIG. 2) of touch zone 256. In implementation other types of tactile sensing technologies employed, controller 52 may perform other functions.

As indicated by step 356, control signals are generated based upon a combination of sensed interactions from both zones 56 and 256. In one implementation, only sliding gestures simultaneously or concurrently received from zones 56 and 256 are sensed and utilized to generate control signals for ultrasound control system 220. For example, in one implementation, control signals may be generated response to a "pinching" motion may be detected by zones 56 and 256, wherein the index finger and the thumb slide along the respective zones 56, 256 so as to converge. Control signals may also be generated response to a "spreading" motion detected by zones 56 and 256, wherein the index finger and the thumb slide along surfaces 56, 256 in divergent directions. In another implementation, sliding gestures that are received within a predefined period of time, one after the other, are sensing utilizing generate control signals for ultrasound control system 220.

In one implementation, in response to sensing such a sliding gesture along touch zone 56 and/or 256, controller 52 generates transducer control signals which are transmitted directly to transducer 50 to adjust the operation of transducer 50 so as to adjust the sensing depth. In another implementation, in response to sensing such a sliding gesture along touch zone 56 and/or zones 56, 256, controller 52 communicates the detected sliding gesture to host 28, wherein controller 36 of host 38 uses the detected sliding gesture(s) to generate transducer control signals which are transmitted to transducer 50 for adjusting the depth of sensing by transducer 50.

In other implementations, particular sliding gestures of a person's finger or fingers along touch zones 56 and/or 256 may correspond to other commands or inputs. For example, in some implementations, such sliding gestures may be utilized by system 20 to cause the presentation of ultrasound results on display 26 to be adjusted. For example, such sliding gestures may be utilized to activate a zoom function or to move a color flow region of interest bounding box (or a bounding box with other type of data being displayed) within a displayed two-dimensional image. In some implementations, other characteristics of probe 230 itself may be adjusted by such a sliding gesture such as a focus, width or direction of emitted and sensed ultrasound pulses.

Figure 6:
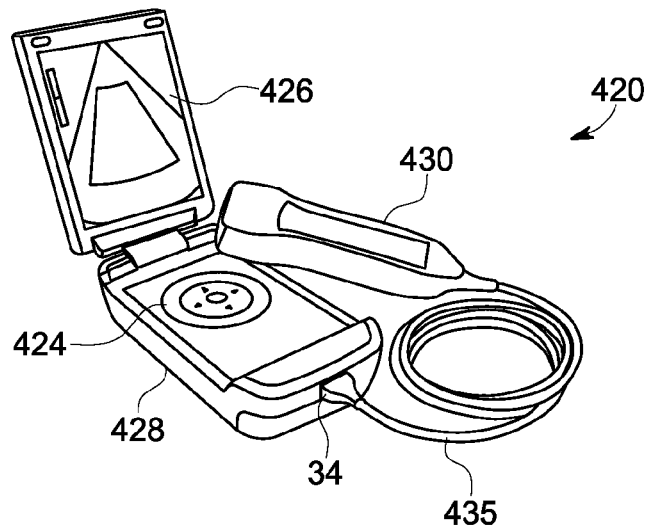
FIG. 6 is a perspective view of another example of the ultrasound sensing system of FIG. 1.
Figure 7:
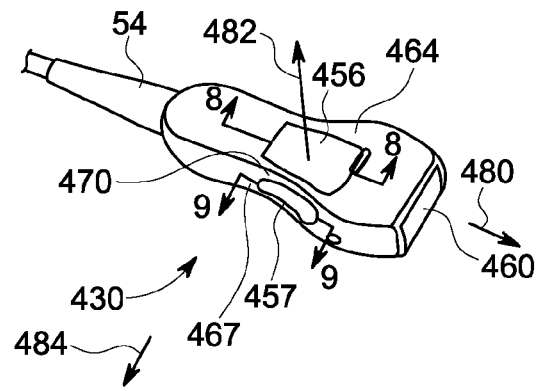
FIG. 7 is a perspective view of a probe of the sensing system of FIG. 6.

FIGS. 6-9 illustrate ultrasound sensing system 420, an example implementation of ultrasound sensing system 220 of FIG. 4. As shown by FIG. 6, ultrasound sensing system 420 comprises input 424, display 426, host 428 and probe 430. Input 424 comprises a device by which a person may provide selections, commands or instructions to host 428. In the example illustrated, input 424 comprises a series of compressible push buttons. In other implementations, input 424 may comprise a keyboard, a mouse, a microphone with speech recognition software, a keypad and the like or may be omitted.

Display 426 comprises a screen or other display by which the results from probe 430 are visibly presented to a caretaker, such as a doctor or nurse. In the example illustrated, display 426 is provided as part of a pivotable screen hinged to host 428. In other implementations, display 426 may comprise a separate screen distinct from host 428 and in communication with host 28 in a wired or wireless fashion.

Host 428 comprises a monitor or other unit which analyzes signals from probe 430 and presents the results of the analysis as well as the signals themselves on display 426. In some implementations, host 428 may additionally at least partially control probe 430.

Host 28 comprises communication interface 34, controller 36 and memory 38, each of which is illustrated and described above with respect to FIG. 1. As shown in FIG. 6, in the example illustrated, host 428 comprise a communication interface 34 which is configured to facilitate communication with probe 430 in a wired fashion using a cable 435. In other implementations, cable 435 may be omitted, where such communication is provided in a wireless fashion.

During operation, controller 36 (shown in FIG. 1 or FIG. 4) of host 428, following instructions contained in memory 38, receives ultrasound echo signals from probe 430 and analyzes such signals, wherein the results of such analysis are presented on display 426. In some implementations, controller 36 may generate control signals adjusting our varying the display of signals and/or results on display 426. In some implementations, controller 36 may further generate control signals adjusting the operation of probe 430. As with system 220, at least a portion of some control functions over probe 430 or over the visible presentation on display 426 are controlled by manual inputs provided on probe 430 itself.

Probe 430 is similar to probe 230. Like probe 230, probe 430 comprises a handheld instrument by which ultrasound waves or pulses are directed into anatomy 40 and by which reflections of such waves are sensed to produce signals which are transmitted to a host such as host 428. Probe 430 provides an intuitive means by which the control of probe 430 and the presentation results on display 26 may be adjusted, permitting a physician or caretaker to focus his or her attention on the patient. Probe 430 comprises transducer 50, controller 52 and communication interface 54, each of which are shown and described above with respect to FIG. 4. In addition, probe 430 comprises touch zones 456 and 457 and a front face or nose 460 adjacent to transducer 50. Touch zones 456 and 457 are each similar to touch zones 56 and 256. In one implementation, each of touch zones 456 and 457 comprising capacitive tactile type sensing areas or regions of surfaces 464, 467, respectively. In the example illustrated, nose 460 and the adjacent transducer 50 face in a first direction 480. Surface 464 and touch zone 456 face in a second direction 482 nonparallel, and nominally perpendicular, to the first direction 480 in which nose 60 and transducer 50 face. Surface 467 and touch zone 457 face in a third direction 44 nonparallel, and nominally perpendicular, to the first direction 480 in which nose 460 and transducer 50 face and also nonparallel, and nominally perpendicular, to the second direction 42 in which surface 464 and touch zone 456 face. As a result, touch zones 456 and 457 facilitate the receipt of sliding gestures from the caretaker's index finger and thumb. In some implementations, because the zones 456 and 457 face outwardly in directions perpendicular to one another, zones 456 and 57 facilitate the entry of commands using different digits while also facilitating the continued gripping and holding of probe 430 in space (solely supported or suspended by the caretaker's hand, not relying upon an underlying surface for support) by the same digits. Separate commands or commands based upon a combination of sliding gestures received from both the finger and the thumb may be entered utilizing zones 456 and 457.

In the example illustrated, touch zones 456 and 457 are spaced apart from one another by an insensitive zone or surface area 470 between surfaces 464 and number 467. As a result, ultrasound sensing system 220 may distinguish between sensed sliding gestures received by touch zone 56 versus those gesture sensed on touch zone 256. In other words, different touch zones may be dedicated to different inputs such that the same gesture may be input to the different zones but may have different results or a different impact depending upon which zone from which the sliding gesture was sensed. In other implementations, touch zones 456 and 457 may be continuous with respect to one another along a surface of probe 430.

Figure 8:
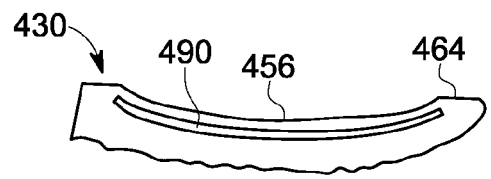
FIG. 8 is a fragmentary sectional view of the probe of FIG. 7 taken along line 8-8.
Figure 9:
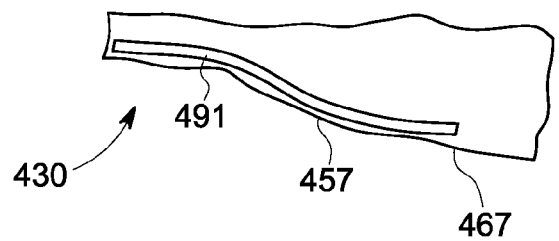
FIG. 9 is a fragmentary sectional view of the probe FIG. 7 taken along line 9-9.

FIGS. 8 and 9 illustrate surfaces 464, 467 and their associated touch zones 456, 457, respectively. As shown by FIG. 8, touch zone 456 includes a tactile sensing device 490 that is below the outermost surface of zone 456. Device 490 may comprise a capacitive type sensing device such as shown in FIG. 2.

As further shown by FIG. 8, touch zone 456 extends along a concave portion of surface 464. As a result, a caretaker may locate his or her digit on touch zone 456 simply by feel and maintenance of the person digit continuously on surface 456 during a sliding gesture is indicated by the concavity of surface 464. In other words, caretaker is tactilely notified of the boundaries of touch zone 456. In other implementations, other tactile characteristics on surface 464 may be used to notify the caretaker of the bounds of touch zone 456. For example, the region of touch zone 456 may alternatively or additionally include such tactile structures such as a smoother or rougher surface as compared to surface 464 outside of touch zone 456 or may include serrations, slight ribbing, bumps, protrusions, dimples and the like indicating the area or the boundary of touch zone 456.

As shown by FIG. 9, touch zone 457 (including tactile sensing device 491) extends along a side portion of probe 430 and along a generally convex portion of surface 467. As with the concave characteristic of touch zone 456, the convex characteristic of touch zone 457 may indicate the proper positioning of a person digit upon touch zone 457. In other implementations, other tactile characteristics on surface 467 may be used to notify the caretaker of the bounds of touch zone 456. For example, the region of touch zone 457 may alternatively or additionally include such tactile structures such as a smoother or rougher surface as compared to forces of surface 464 outside of touch zone 456 or may include serrations, slight ribbing, bumps, protrusions, dimples and the like indicating the boundary of touch zone 457. Example of bumps or protrusions are shown on surface 556 of probe 530C in FIG. 12.

Figure 10:
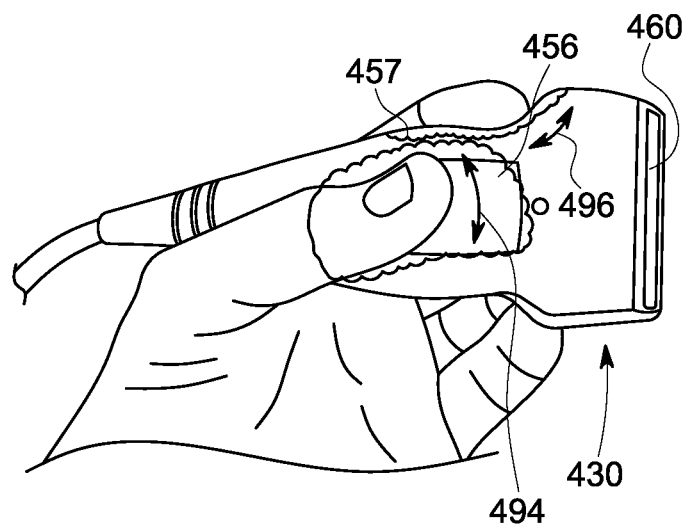
FIG. 10 is a perspective view of the probe of FIG. 7 being manipulated in a first fashion.
Figure 11:
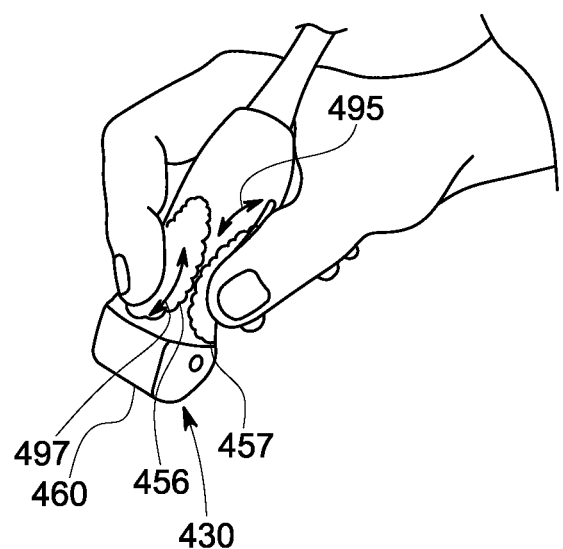
FIG. 11 is a perspective view of the probe of FIG. 7 the manipulated in an alternative second fashion.

FIGS. 10 and 11 illustrate different gripping of probe 430 and the location of a caretaker's index finger and thumb upon the different touch zones 456, 457. In FIG. 10, probe 430 is gripped such that the caretaker thumb resides upon zone 456 while the person's index finger resides upon and against touch zone 457. Arrows 494 in FIG. 10 illustrate one example path or motion for the caretaker thumb against touch zone 456 to adjust the operation of ultrasound sensing system 430. Arrows 496 illustrate one example path or motion for the caretaker's index finger along and in contact with touch zone 457 to adjust the operation of ultrasound sensing system 420.

In FIG. 11, probe 430 is gripped such that the person's thumb resides on and against touch zone 457 of the caretaker's index finger reside on and against touch zone 456. Arrows 495 in FIG. 11 illustrate one example path or motion for the caretaker thumb against touch zone 457 to adjust the operation of ultrasound sensing system 430. Arrows 497 illustrate one example path or motion for the caretaker's index finger along and in contact with touch zone 456 to adjust the operation of ultrasound sensing system 420. In other implementations, other passive motion by the caretaker's digits along touch zones 456, 457 may be utilized to input adjustments or commands to ultrasound sensing system 420.

Figure 12:
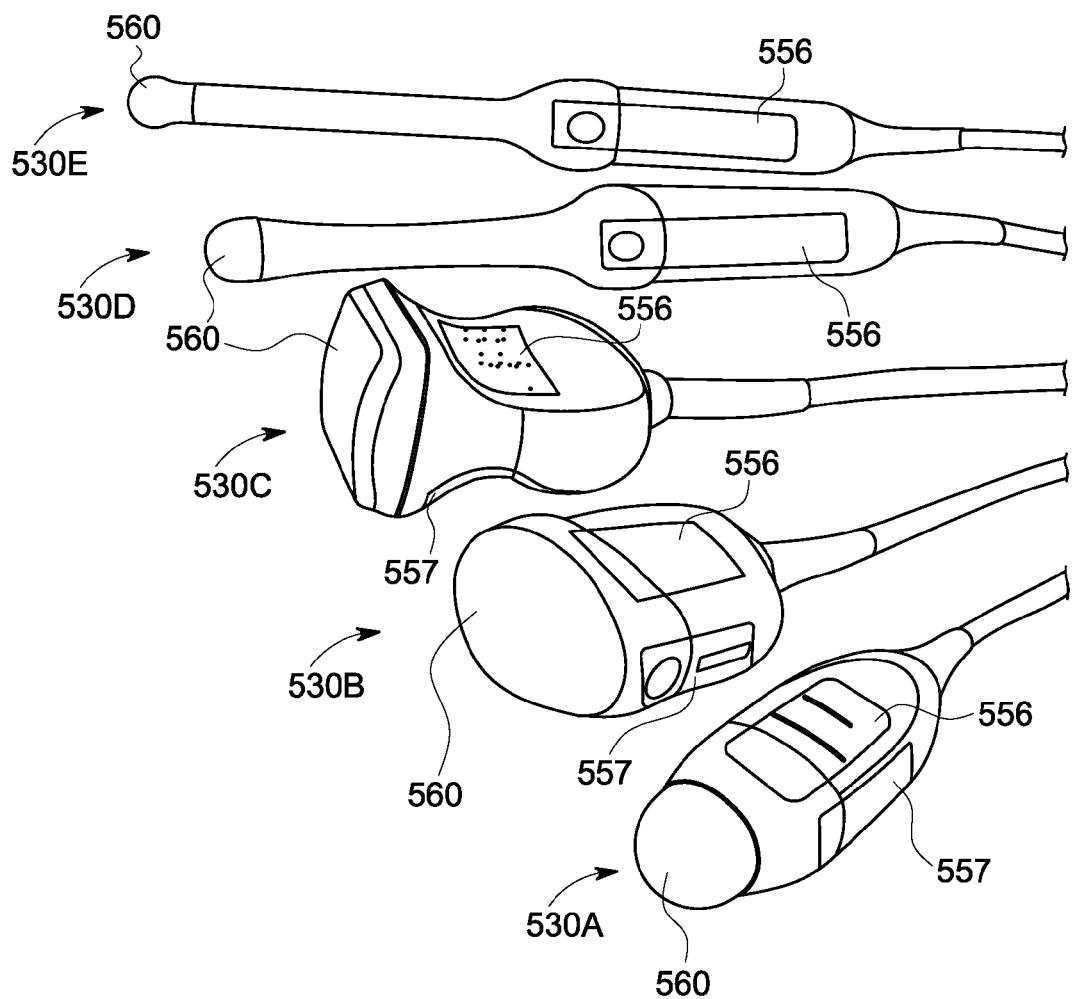
FIG. 12 is a perspective view of alternative example probes.

FIG. 12 illustrates probes 530A, 530B, 530C, 530D and 530E (collectively referred to as probes 530), alternative implementations of probe 430. Each of probes 530 comprises a handheld instrument by which ultrasound waves or pulses are directed into anatomy 40 and by which reflections of such waves are sensed to produce signals which are transmitted to a host such as host 428. Each of probes 530 provides an intuitive means by which the control of the particular probe 530 and the presentation results on display 26 may be adjusted, permitting a physician or caretaker to focus his or her attention on the patient. Each of probes 530 comprises transducer 50, controller 52 and communication interface 54, each of which are shown and described above with respect to FIG. 4. In addition, each of probes comprises such zones 556 and 557 and a front face or nose 560 adjacent to transducer 50. Touch zones 556 and 557 are each similar to touch zones 56 and 256. In one implementation, each of touch zones 556 and 557 comprising capacitive tactile type sensing areas or regions of surfaces 564, 567, respectively.

Similar to probe 430, probes 530A and 530B have touch zones 556 and 557 which face in directions perpendicular to one another. Probes 530C, 530D and 530E are similar to probes 530A and 530B except that touch zones 556 and 557 indirectly opposite directions on obsolete facing surfaces by 56 and 557 of such probes, both of such touch zones 556 and 557 of probes 530C, 530D and 530E facing in directions perpendicular to the direction of nose 560. As a result, touch zones 556 and 557 of probes 530C, 530D and 530E facilitate secure gripping and holding of such probes with the caretaker's thumb and index finger be located on opposite sides (180° apart) of the handle portions of such probes. It should be noted that although only touch zones 556 are viewable on probes 530D and 530E, touch zones 557 are identical to touch zones 556 but extend on an opposite sides of such probes with respect to such zones 556.

Although the present disclosure has been described with reference to example embodiments, workers skilled in the art will recognize that changes may be made in form and detail without departing from the spirit and scope of the claimed subject matter. For example, although different example embodiments may have been described as including one or more features providing one or more benefits, it is contemplated that the described features may be interchanged with one another or alternatively be combined with one another in the described example embodiments or in other alternative embodiments. Because the technology of the present disclosure is relatively complex, not all changes in the technology are foreseeable. The present disclosure described with reference to the example embodiments and set forth in the following claims is manifestly intended to be as broad as possible. For example, unless specifically otherwise noted, the claims reciting a single particular element also encompass a plurality of such particular elements.

What is claimed is:

1. An apparatus comprising:
    an ultrasound probe comprising:
    a body terminating at a nose;
    an ultrasound transducer adjacent the nose and facing in a first direction; and
    a first touchpad zone to detect a sliding gesture of a first digit, the first touchpad zone extending along a first surface facing in a second direction perpendicular to the first direction;
    a second touchpad zone to detect a sliding gesture of a second digit, the second touchpad zone extending along a second surface facing a third direction perpendicular to the first direction and perpendicular to the second direction; and
    a controller to receive sensed signals from the first touchpad zone in response to detection of the sliding gesture of the first digit and to receive sensed signals from the second touchpad zone in response to detection of the sliding gesture of the second digit, wherein the controller is configured to generate first control signals in response to a detected sliding motion of the first digit across the first touchpad zone and to generate second control signals in response to a detected sliding motion of the second digit across the second touchpad zone.

2. The apparatus of claim 1, wherein the first digit comprises a thumb and the second digit comprises an index finger.

3. The apparatus of claim 1, wherein the first touchpad zone and the second touchpad zone are spaced by an insensitive zone.

4. The apparatus of claim 1, wherein the first surface is concave forming a concavity having boundaries corresponding to boundaries of the first touchpad zone.

5. The apparatus of claim 4, wherein the second surface is concave forming a second concavity having boundaries corresponding to boundaries of the second touchpad zone.

6. The apparatus of claim 1 further comprising:
    a third surface opposite the first surface, the third surface facing in a fourth direction perpendicular to the first direction and perpendicular to the third direction; and
    a fourth surface opposite the second surface, the fourth surface facing in a fifth direction perpendicular to the first direction and perpendicular to the fourth direction.

7. The apparatus of claim 1 further comprising:
    a display;
    wherein the controller is configured to receive ultrasonic echo signals from the probe and to generate display control signals based on such echo signals, wherein the display presents an image in response to the control signals.

8. The apparatus of claim 1 wherein the controller is configured to generate control signals causing the ultrasound transducer to change a characteristic of at least one of emitted ultrasound waves and sensed ultrasound echoes in response to the sensed sliding motion.

9. The apparatus of claim 8, wherein a depth of ultrasound sensing changes in response to the control signals.

10. The apparatus of claim 1, wherein the controller is configured to generate control signals to adjust an active operating sensing characteristic of the ultrasound probe or a presentation of display results based upon a combination of sensed digit interactions with the first touchpad zone and the second touchpad zone, wherein the control signals are based upon detection of at least one of a direction and shape of a sliding motion of the first digit across the first touchpad zone and detection of at least one of a direction and shape of a sliding motion of the second digit across a second touchpad zone.

11. The apparatus of claim 10, wherein the sensed digit interactions are concurrent.

12. The apparatus of claim 1, wherein the controller is configured to implement a first operational setting upon completion of a first sliding gesture of the first digit that terminates at a first location on the first touchpad zone and upon completion of a second sliding gesture of the second digit that terminates at a second location on the second touchpad zone and wherein the controller is configured to implement a second operational setting, different than the first operational setting, upon completion of a third sliding gesture of the first digit that terminates at the first location on the first touchpad zone and completion of a fourth sliding gesture of the second digit that terminates at the second location on the second touchpad zone.

13. The apparatus of claim 1, wherein the controller is configured to generate first control signals in response to a detected pinching together of sliding motion of the first digit across the first touchpad zone and sliding motion of the second digit across the second touchpad zone and to generate second control signals in response to a detected spreading apart of sliding motion of the first digit across a first touchpad zone and sliding motion of the second digit across the second touchpad zone.

14. The apparatus of claim 1 further comprising a controller to receive sensed signals from the first touchpad zone, wherein the controller configured to identify a shape of the sliding gesture of the first digit across the first touchpad zone and to generate control signals to implement an operational setting assigned to the identified shape.

15. The apparatus of claim 1, wherein the controller is configured to implement a first operational setting upon completion of a first sliding gesture that terminates at a location on the first touchpad zone and wherein the controller is configured to implement a second operational setting, different than the first operational setting, upon completion of a second sliding gesture that terminates at the location on the first touchpad zone.

16. The apparatus of claim 1, wherein the first touchpad zone is configured to distinguish between a sliding gesture of the first digit and taps of the first digit.

17. An apparatus comprising:
a non-transient computer-readable medium containing computer-readable code to direct a processor to:
receive first sensed signals from a first touchpad zone of an ultrasound probe in response to a first interaction of a first digit with the first touchpad zone;
receive second sensed signals from a second touchpad zone of the ultrasound probe in response to second interaction of a second digit with the second touchpad zone; and
generate control signals to adjust one of an active operating sensing characteristic of the ultrasound probe or a presentation of display results based upon a combination of the first interaction with the first touchpad zone and the second interaction with the second touchpad zone, wherein the control signals are based upon detection of at least one of a direction and shape of a sliding motion of the first digit across the first touchpad zone and detection of at least one of a direction and shape of a sliding motion of the second digit across a second touchpad zone.

18. A method comprising:
receiving first sensed signals from a first touchpad zone of an ultrasound probe in response to a first interaction of a first digit with the first touchpad zone, the first sensed signals indicating at least one of a direction and shape of the first digit across the first touchpad zone;
receiving second sensed signals from a second touchpad zone of the ultrasound probe in response to second interaction of a second digit with the second touchpad zone, the second sensed signals indicating at least one of a direction and shape of the first digit across the first touchpad zone; and
generating control signals to adjust one of an active operating sensing characteristic of the ultrasound probe or a presentation of display results based upon a combination of a detected one of the direction and shape of the first interaction with the first touchpad zone and a detected at least one of the direction and shape of the second interaction with the second touchpad zone.

19. The method of claim 18, wherein the first interaction comprises a sliding motion of the first digit across the first touchpad zone, wherein the second interaction comprises a sliding motion of the second digit across the second touchpad zone, wherein the control signals are based upon a combination of a detected direction of the sliding motion of the first digit relative to a detected direction of the sliding motion of the second digit.

20. The method of claim 19, wherein first control signals are generated in response to a detected pinching together of sliding motion of the first digit across the first touchpad zone and sliding motion of the second digit across the second touchpad zone and wherein second control signals are generated in response to a detected spreading apart of sliding motion of the first digit across a first touchpad zone and a sliding motion of the second digit across the second touchpad zone.

21. The method of claim 19, further comprising tactilely identifying a boundary of the first touchpad zone on a surface of the ultrasound probe.

22. The method of claim 19, wherein first control signals are generated based upon a detected sliding motion of the first digit across the first touchpad zone along a first path and second control signals are generated based upon a detected sliding motion of the first digit across the first touchpad zone along a second path orthogonal to the first path.

* * * * *